| United States Patent [19] | [11] Patent Number: 4,935,424 |
|---|---|
| Caprathe et al. | [45] Date of Patent: Jun. 19, 1990 |

[54] 4 OR 5-(SUBSTITUTED PIPERAZINYLALKYL)-2-AMINO-THIAZOLES AS ANTIPSYCHOTIC AGENTS

[75] Inventors: Bradley W. Caprathe, Redford; Juan C. Jaen, Plymouth; Lawrence D. Wise, Ann Arbor, all of Mich.

[73] Assignee: Warner-Lambert Company, Morris Plains, N.J.

[21] Appl. No.: 199,898

[22] Filed: May 27, 1988

[51] Int. Cl.$^5$ .................. A61K 31/495; A61K 31/44; A61K 31/405; C07D 417/14; C07D 405/14; C07D 409/14

[52] U.S. Cl. .................. 514/252; 514/255; 514/256; 514/269; 514/274; 514/333; 514/342; 544/295; 544/316; 544/319; 544/333; 544/357; 544/364; 544/369; 544/379; 544/405; 546/256; 546/280

[58] Field of Search .................. 544/364, 369, 379; 514/252

[56] References Cited

U.S. PATENT DOCUMENTS

| 3,821,234 | 6/1974 | Koppe et al. | 260/295 |
|---|---|---|---|
| 4,018,786 | 4/1977 | Amselem | 260/206.7 |
| 4,564,678 | 1/1986 | Tomiyama | 544/367 |
| 4,737,500 | 4/1988 | Sorg | 544/364 |

FOREIGN PATENT DOCUMENTS

| 0032058 | 7/1981 | European Pat. Off. |
|---|---|---|
| 2536399 | 10/1983 | France. |
| 1149110 | 10/1968 | United Kingdom. |

OTHER PUBLICATIONS

Dodson et al, JACS 67(1945), pp. 2242-2243.
King et al, JACS 69(1947), pp. 1813-1814.
Sczycinski et al, Chem. Abst. 95-97851a (1981).
Chemical Abstracts, vol. 95, No. 11, Sep. 14, 1981.
European Journal of Medicinal Chemistry, Chimica Therapeutica, vol. XI, No. 1, 49, Jan./Feb. 1976.
PCT International Search Report PCT/US89/02273.
Farmaco, Ed. Sci., 1986, 41(6), 483-98, Acta Polon. Pharm. XL, NR 2, 1983, pp. 159-170.

*Primary Examiner*—Cecilia Shen
*Attorney, Agent, or Firm*—Francis J. Tinney

[57] ABSTRACT

Substituted 2-aminothiazoles are described, as well as methods for the preparation and pharmaceutical compositions of same, which are useful as dopamine agonists with selectivity for the presynaptic dopamine receptor and are useful as dopaminergic, antipsychotic, and antihypertensive agents as well as for treating hyperprolactinaemia-related conditions and central nervous system disorders.

10 Claims, No Drawings

4 OR 5-(SUBSTITUTED PIPERAZINYLALKYL)-2-AMINOTHIAZOLES AS ANTIPSYCHOTIC AGENTS

BACKGROUND OF THE INVENTION

The present invention relates to novel substituted 2-aminothiazoles useful as pharmaceutical agents, to methods for their production, to pharmaceutical compositions which include these compounds, and a pharmaceutically acceptable carrier, and to pharmaceutical methods of treatment. More particularly, the novel compounds of the present invention are dopamine agonists having selectivity for the presynaptic dopamine receptor, i e., an autoreceptor. The advantage of an autoreceptor agonist is that it modulates the activity of dopaminergic systems selectively, without the postsynaptic stimulation which is inherent to nonselective dopamine agonists.

Compounds of formula A

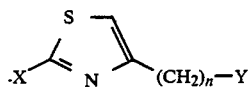

wherein X represents amino, acylamino, guanidino, and N,N-di-lower-aminomethyleneamino; n is an integer from 1 to 3; and Y represents

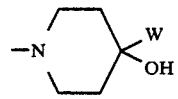

wherein W is phenyl or substituted phenyl,

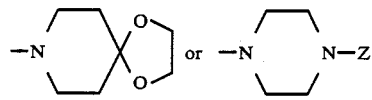

wherein Z is carboxy lower alkyl are disclosed in U.S. Pat. No. 4,564,678 as having antigastric secretion activity.

Compounds of formula B

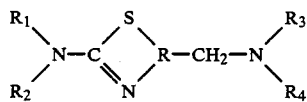

wherein R is a group of formula:

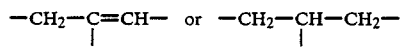

linked with the sulfur atom by its second carbon atom are disclosed in U.S. Pat. No. 4,018,786 as having hypocholesterolemic and antiinflammatory activity.

Compounds of formula C

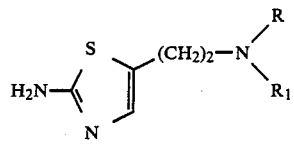

are described by Vitali, T., et al, *Farmaco. Ed. Sci,* vol. 41, pages 483–498 (1986) as gastric secretion stimulants.

Compounds of formula D

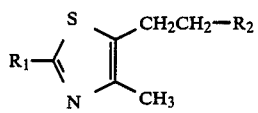

wherein $R_1$ is hydrogen, $-SCH_3$ or $-S-C_2H_5$; and $R_2$ is

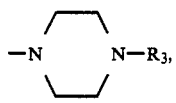

where $R_3$ is methyl, phenyl, substituted phenyl, 2-pyridyl, or $-CO_2C_2H_5$,

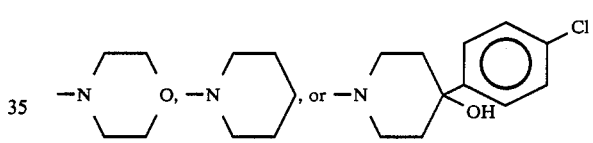

are described by Bogdal, M., et al, *Acta Polon. Pharm. XL,* 1983(2), pages 159–170.

A series of 1-(thiazolyl-5-alkyl)-4-(pyridyl-2)piperazines which exhibit blood pressure lowering and CNS activity is disclosed in British Patent No. 1,149,110.

A series of substituted piperidine derivatives which exhibit tranquilizing activity is disclosed in U.S. Pat. No. 3,821,234.

However, none of the thiazoles disclosed in the aforementioned references suggest the combination of structural variations of the compounds of the present invention described hereinafter. Furthermore, the aforementioned thiazole derivatives are not disclosed as dopamione agonists having selectivity for the presynaptic dopamine receptor.

SUMMARY OF THE INVENTION

Accordingly, the present invention is a compound of Formula I

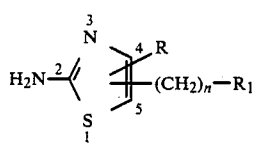

wherein R is hydrogen or lower alkyl; n is an integer from 2 to 5, $R_1$ is

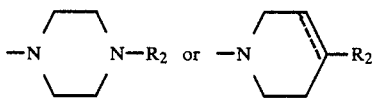

wherein R₂ is phenyl, phenyl substituted by lower alkyl, lower alkoxy, lower thioalkoxy, halogen, or trifluromethyl, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen; ⎓ is a single or double bond; and either R or —(CH₂)$_n$—R₁ is attached at the 4 or 5 position; or a pharmaceutically acceptable acid addition salt thereof, with the exclusion of a compound of formula

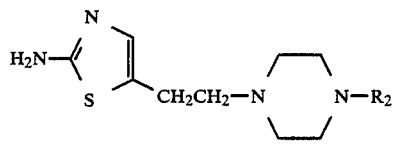

wherein R₂ is phenyl or phenyl substituted by halogen

As dopamine agonists with selectivity for the presynaptic dopamine receptor, the compounds of Formula I are useful as antipsychotic agents for treating psychoses, such as schizophrenia. They are also useful as antihypertensives and for the treatment of disorders which respond to dopaminergic activation. Thus, other embodiments of the present invention include the treatment, by a compound of Formula I, of hyperprolactinaemia-related conditions, such as galactorrhea, amenorrhea, menstrual disorders and sexual dysfunction, and several central nervous system disorders such as Parkinson's disease, Huntington's chorea, and depression.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

"Lower alkoxy" and "thioalkoxy" are O-alkyl or S-alkyl of from one to six carbon atoms as defined above for "lower alkyl."

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, and the like.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorus, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science,* Vol. 66, pages 1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated as well as solvated forms, including hydrated forms. In general, the solvated forms, including hydrated forms, are equivalent to unsolvated forms and are intended to be encompassed within the scope of the present invention.

A preferred compound of Formula I is one wherein n is an integer from 2 to 4, R is hydrogen, methyl or ethyl, and R₁ is

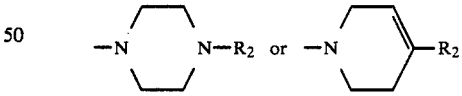

Another preferred embodiment is a compound of Formula I wherein R₂ is phenyl, 2-pyridinyl, or 2-pyrimidinyl.

Particularly valuable are:
4-methyl-5-[3-[4-(2-pyrimidinyl)-1-piperazinyl]propyl]-2-thiazolamine;
4-[4-[4-(2-pyrimidinyl)-1-piperazinyl]butyl]-2-thiazolamine;
4-methyl-5-[2-(4-phenyl-1-piperazinyl)ethyl]-2-thiazolamine;
4-[3-(4-phenyl-1-piperazinyl)propyl]-2-thiazolamine;
5-[2-(3,6-dihydro-4-phenyl-1(2H)-pyridinyl)ethyl]-4-methyl-2-thiazolamine;
4-[3-(3,6-dihydro-4-phenyl-1(2H)-pyridinyl)propyl]-2-thiazolamine;

4-methyl-5-[2-[4-(2-pyrimidinyl)-1-piperazinyl]ethyl]-2-thiazolamine;

4-[3-[4-(2-pyrimidinyl)-1-piperazinyl]propyl]-2-thiazolamine;

4-methyl-5-[2-[4-(2-pyridinyl)-1-piperazinyl]-ethyl-2-thiazolamine;

4-[3-[4-(2-pyridinyl)-1-piperazinyl]propyl]-2-thiazolamine;

4-methyl-5-[3-[4-(2-pyridinyl)-1-piperazinyl]propyl]-2-thiazolamine;

4-[4-[4-(2-pyridinyl)-1-piperazinyl]butyl]-2-thiazolamine;

5-[2-[4-(2-pyridinyl)-1-piperazinyl]ethyl]-2-thiazolamine;

5-[2-(3,6-dihydro-4-phenyl-1-(2H)-pyridinyl)ethyl]-2-thiazolamine;

5-[2-(4-phenyl-1-piperazinyl)ethyl]-2-thiazolamine; or a pharmaceutically acceptable acid addition salt thereof.

A compound of the Formula I

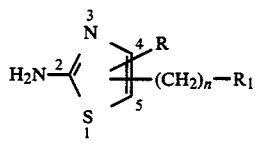

wherein R is hydrogen or lower alkyl; n is an integer from 2 to 5; $R_1$ is

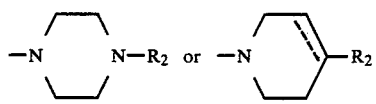

wherein $R_2$ is phenyl, phenyl substituted by lower alkyl, lower alkoxy, lower thioalkoxy, halogen, or trifluoromethyl, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen; ――― is a single or double bond; and either R or —(CH$_2$)$_n$—R$_1$ attached at the 4 or 5 position; or a pharmaceutically acceptable acid addition salt thereof, with the exclusion of a compound of formula

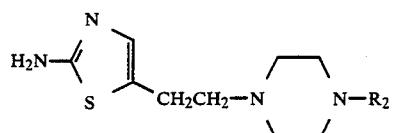

wherein $R_2$ is phenyl or phenyl substituted by halogen, may be prepared by reacting a compound of Formula IIa

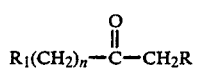

wherein R, $R_1$, and n are as defined above with thiourea in the presence of an oxidizing agent such as a halogen, sulfuryl chloride, thionyl chloride, chlorosulfonic acid, sulfur monochloride, and the like using the methodology described by Dodson, R. M. and King, L. C, *Journal of American Chemical Society*, Vol. 67, pages 2242–2243 (1945) and Vol. 68, page 871 (1946) or formamidine disulfide dihydrochloride using the methodology described by King, L. C. and Ryden, I., *Journal of American Chemical Society*, Vol. 69, pages 1813–1814 (1947) to afford a mixture, resulting from ring formation on either methylene group adjacent to the carbonyl group in a compound of Formula IIa, of a compound of Formula IA and Formula Ic

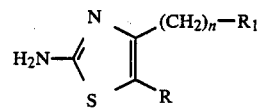

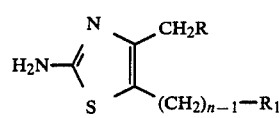

wherein R, $R_1$, and n are as defined above. The aforementioned mixture is separated by conventional methodology to afford a compound of Formula Ia. preferably the reaction is carried out using thiourea and iodine and the resulting mixture separated by chromatography over silica gel.

Reaction of a compound of Formula IIb,

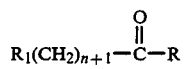

wherein R, $R_1$, and n are as defined above with thiourea, in the presence of an oxidizing agent or formamidine disulfide dihydrochloride by following the same procedure used to prepare a compound of Formula Ia affords a mixture, resulting from ring formation on either methylene group adjacent to the carbonyl group in a compound of Formula IIb, of a compound of Formula Ib, wherein R, $R_1$, and n are as defined above and a compound of Formula Id, wherein R$^a$ is hydrogen or lower alkyl of one to five carbon atoms and $R_1$, and n are as defined above,

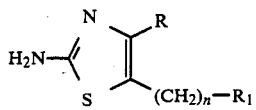

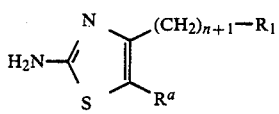

except that when R in a compound of Formula IIb is hydrogen only a compound of Formula Ib is formed wherein R is hydrogen and $R_1$ and n are as defined above. The aforementioned mixture is separated by conventional methodology to afford a compound of Formula Ib.

For certain values of R and $R_1$, a compound of Formula Ic is equivalent to a compound of Formula Ib. Also, for certain values of R$^a$, R, $R_1$, and n a compound of Formula Id is equivalent to a compound of Formula Ia.

A compound of Formula IIa is prepared by reacting a compound of Formula IIIa

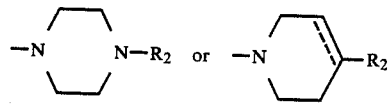   IIIa wherein X is a halogen or other suitable leaving group such as, for example, para-toluenesulfonyloxy and the like, preferably X is chlorine or bromine, and R and n are as defined above with a compound of Formula IV $R_1H$   IV wherein $R_1$ is

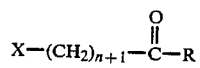

wherein $R_2$ and ----- are as defined above in the presence of a base such as an alkali or alkaline-earth metal hydroxide, carbonate or bicarbonate, for example, sodium hydroxide, potassium carbonate, sodium bicarbonate, calcium hydroxide, calcium carbonate, and the like, or an organic amine, for example, triethylamine, in an inert solvent, such as, for example, an alcohol, for example, methanol, ethanol and the like, dimethylformamide and the like, and mixtures thereof at about 25° C. to about the reflux temperature of the solvent or solvents. Preferably, the reaction is carried out in a mixture of ethanol and dimethylformamide in the presence of sodium bicarbonate at reflux to give a compound of Formula IIa.

A compound of Formula IIb is prepared by reacting a compound of Formula IIIb

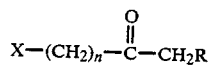   IIIb wherein X is a halogen or other suitable leaving group such as, for example, para-toluenesulfonyloxy and the like, preferably X is chlorine or bromine, and R and n are as defined above with a compound of Formula IV $R_1H$   IV wherein $R_1$ is as defined above by following the same procedure used to prepare a compound of Formula IIa.

Compounds of Formulas IIIa, IIIb, and IV are either known or capable of being prepared by methods known in the art.

Alternatively, a compound of the Formula I is prepared by reacting a compound of Formula IIIa

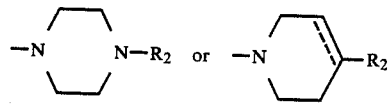   IIIa wherein X is halogen or other suitable leaving group such as, for example, para-toluenesulfonyloxy, and the like, preferably chlorine or bromine, and R and n are as defined above with thiourea, in the presence of an oxidizing agent or formamidine disulfide dihydrochloride by following the same procedure used to prepare a compound of Formula Ia to afford a mixture of a compound of Formula Va and Formula Vc

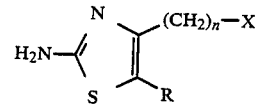   Va

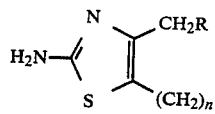   Vc wherein R, n, and X are as defined above. The aforementioned mixture may be optionally separated by conventional methodology, for example, chromatography over silica gel or used directly in the next step. Preferably, the reaction is carried out using thiourea and iodine.

A compound of Formula Va or the mixture of a compound of Formula Va and a compound of Formula Vc is reacted with a compound of Formula IV $R_1H$   IV wherein $R_1$ is as defined above in the presence of a base such as an alkali of alkaline-earth metal carbonate or bicarbonate, for example, potassium carbonate, sodium bicarbonate, and the like, in an inert solvent, such as, for example, an alcohol, for example, methanol, ethanol, and the like, dimethylformamide, acetonitrile, chloroform, and the like and mixtures thereof at about 25° C. to about the reflux temperature of the solvent or solvents. Preferably, the reaction is carried out in dimethylformamide at about 80°-90° C. to give a compound of Formula Ia.

In the case where the mixture of a compound of Formula Va and a compound of Formula Vc is reacted with a compound of Formula IV, the resulting mixture is separated by conventional methodology as described above to afford a compound of Formula Ia.

Reaction of a compound of Formula IIIb

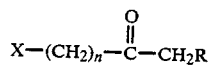   IIIb wherein X, R, and n are as defined above with thiourea, in the presence of an oxidizing agent or formamidine disulfide dihydrochloride by following the same procedure used to prepare a compound of Formula Va affords a mixture of a compound of Formula Vb,

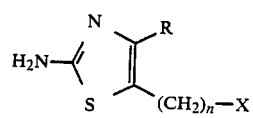   Vb

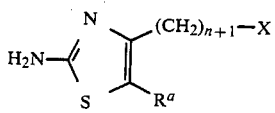   Vd wherein R, n, and X are as defined above and a compound of Formula Vd, wherein $R^a$ is hydrogen or lower alkyl of one to five carbon atoms and n and X are as defined above, except that when R in a compound of Formula IIIb is hydrogen, only a compound of Formula Vb is formed wherein R is hydrogen and n and X are as defined above.

For certain values of R and n, a compound of Formula Vc is equivalent to a compound of Formula Vb. Also, for certain values of $R^a$, R, and n a compound of Formula Vd is equivalent to a compound of Formula Va.

A compound of Formula Vb or the mixture of a compound of Formula Vb and Formula Vd is reacted with a compound of Formula IV $$R_1H \quad \text{IV}$$

wherein R is as defined above in the presence of a base and an inert solvent by following the same procedure used to prepare a compound of Formula Ia to afford a compound of Formula Ib.

Preferably a compound of Formula Ia wherein R is hydrogen, and n and R are as defined above is prepared by reacting a compound of Formula VI

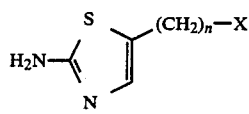
VI wherein X is chlorine or bromine and n is as defined above with a compound of Formula IV $$R_1H \quad \text{IV}$$

wherein $R_1$ is as defined above by following the same procedure used to prepare a compound of Formula Ia from a compound of Formula Va.

A compound of Formula VI is prepared by reacting a compound of Formula VII

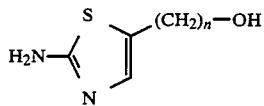
VII wherein n is as defined above with thionyl chloride, thionyl bromide, and the like in an inert solvent such as chloroform and the like at about 25° C. to the reflux temperature of the solvent. Preferably, the reaction is carried out in chloroform at reflux to give a compound of Formula VI.

A compound of Formula VII is prepared by reacting a compound of Formula VIII

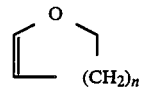
VIII wherein n is one to four with N-bromosuccinimide in water at about 0° C. under a nitrogen atmosphere followed by thiourea, refluxing overnight and neutralization with a base such as ammonium hydroxide and the like to give a compound of Formula VII.

A compound of Formula VIII is either known or capable of being prepared by methods known in the art.

The compounds of Formula I are valuable dopaminergic agents The tests employed indicate that compounds of Formula I possess dopamine agonist activity with selectivity for the presynaptic dopamine receptor (autoreceptor). Thus, the compounds of Formula I were tested for their ability to inhibit locomotor activity in mice according to the assay described in *Pharmacol. Biochem. Behav.* 1978 (8) 97; for their ability to inhibit haloperidol binding in a receptor binding assay described in *Mol. Pharmacol.* 1976 (12), 800; for their ability to inhibit brain dopamine synthesis in rats according to the protocol described in *Naumyn-Schmiedeberg's Arch. Pharmacol.*, 1976 (296) 5; and for their ability to inhibit dopamine neuron firing in rats according to the protocol described in *Nature New Biology,* 1973 (245) 123. The above test methods are incorporated herein by reference The data in the table shows the selective presynaptic dopamine agonist activity of representative compounds of Formula I.

| Example Number | Compound | Inhibition of Haloperidol Binding ($IC_{50}$ nM) | Inhibition of Locomotor Activity in Mice ($ED_{50}$ mg/kg, IP) | Inhibition of Dopamine Synthesis in Rats | Inhibition of Dopamine Neuron Firing in Rats |
|---|---|---|---|---|---|
| 1 | 4-Methyl-5-[3-[4-(2-pyrimidinyl)-1-piperazinyl]-propyl]-2-thiazolamine | 370 | 6.3 | 82% at 1 mg/kg, IP | 90% at 2.5 mg/kg, IP |
| 1a | 4-[4-[4-(2-Pyrimidinyl)-1-piperazinyl]-butyl]-2-thiazolamine | 1060 | >30 | | |
| 1b | 4-Methyl-5-[2-(4-phenyl-1-piperazinyl)-ethyl]-2-thiazolamine | 100% at 10,000 nM | 1.5 | | 80% at 10 mg/kg, IP |
| 1c | 4-[3-(4-Phenyl-1-piperazinyl)propyl]-2-thiazolamine | 40% at 10,000 nM | 2.4 | | |
| 1d | 5-[2-(3,6-Dihydro-4-phenyl-1(2H)-pyridinyl)ethyl]-4-methyl-2-thiazolamine | 400 | 0.88 | 84% at 10 mg/kg, IP | 70% at 2.5 mg/kg, IP |
| 1e | 4-[3-(3,6-Dihydro-4-phenyl-1(2H)-pyridinyl)propyl]-2-thiazolamine, dihydrochloride | 346 | 1.7 | 44% at 10 mg/kg, IP | 78% at 2.5 mg/kg, IP |
| 1f | 4-Methyl-5-[2-[4-(2-pyrimidinyl)-1-piperazinyl]ethyl]-2-thiazolamine | 118 | 1.4 | | |
| 1g | 4-[3-[4-(2-Pyrimidinyl)-1-piperazinyl]-propyl]-2-thiazolamine | 1600 | >30 | | |
| 1h | 4-Methyl-5-[2-[4-(2-pyridinyl)-1-piperazinyl]ethyl]-2-thiazolamine | 75 | 1.4 | 87% at 1 mg/kg, IP | 100% at 2.5 mg/kg, IP |
| 1i | 4-[3-[4-(2-Pyridinyl)-1-piperazinyl]-propyl]-2-thiazolamine | 100% at 10,000 nM | 7.6 | 43% at 10 mg/kg, IP | |

-continued

| Example Number | Compound | Inhibition of Haloperidol Binding ($IC_{50}$ nM) | Inhibition of Locomotor Activity in Mice ($ED_{50}$ mg/kg, IP) | Inhibition of Dopamine Synthesis in Rats | Inhibition of Dopamine Neuron Firing in Rats |
|---|---|---|---|---|---|
| 1j | 4-Methyl-5-[3-[4-(2-Pyridinyl)-1-piperazinyl]propyl]-2-thiazolamine | 249 | 4.6 | 100% at 10 mg/kg, IP | 98% at 2.5 mg/kg, IP |
| 1k | 4-[4-[4-(2-Pyridinyl)-1-piperazinyl]-butyl]-2-thiazolamine | 488 | 5.5 | 63% at 10 mg/kg, IP | |
| | 5-[2-[4-(2-Pyridinyl)-1-piperazinyl]-ethyl-2-thiazolamine | | 5.9 | 92% at 10 mg/kg, IP | |
| 2a | 5-[2-[4-Phenyl-1-piperazinyl)ethyl]-2-thiazolamine | | 2.6 | | |
| 2b | 5-[2-(3,6-Dihydro-4-phenyl-1-(2H)-pyridinyl)ethyl]-2-thiazolamine | | 0.47 | 25% at 10 mg/kg, IP | |

The compounds of the present invention can be prepared and administered in a wide variety of oral and parenteral dosage forms. It will be obvious to those skilled in the art that the following dosage forms may comprise as the active component, either a compound of Formula I, a corresponding pharmaceutically acceptable salt of a compound of Formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material In powders, the carrier is a finely divided solid which is in admixture with the finely divided active compound. In the tablet, the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low-melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms The quantity of active compound in a unit dose of preparation may be varied or adjusted from 1 mg to 100 mg according to the particular application and the potency of the active ingredient.

In therapeutic use as antipsychotic agents, the compounds utilized in the pharmaceutical method of this invention are administered at the initial dosage of about 1 mg to about 50 mg per kilogram daily. A daily dose range of about 5 mg to about 20 mg per kilogram is preferred.

The dosages, however, may be varied depending upon the requirements of the patients, the severity of the condition being treated, and the compound being employed. Determination of the proper dosage for a particular situation is within the skill of the art. Generally, treatment is initiated with smaller dosages which are less than the optimum dose of the compound Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

4-Methyl-5-[3-[4-(2-pyrimidinyl)-1-piperazinyl]-propyl]-2-thiazolamine

EXAMPLE 1a

4-[4-[4-(2-Pyrimidinyl)-1-piperazinyl]butyl]-2-thiazolamine

Iodine, 6.34 g, is added in small portions to a mixture of 6 g of 6-[4-(2-pyrimidinyl)-1-piperazinyl]-2-hexanone (Example A) and 3.8 g of thiourea. The resulting paste is heated at 110° C. overnight. The mixture is taken up into boiling water, filtered, and basified with ammonium hydroxide. Dichloromethane is used to extract the products which are purified by silica gel chromatography to afford 2 g of recovered starting ketone, 0.8 g of 4-methyl-5-[3-[4-(2-pyrimidinyl)-1-piperazinyl]propyl]-2-thiazolamine (Example 1); mp 152°–156° C.; and 1.2 g of 4-[4-[4-(2-pyrimidinyl)-1-piperazinyl]butyl]-2-thiazolamine (Example 1a); mp 101°–104° C.

In a process analogous to Example 1 and Example 1a using appropriate starting materials the corresponding compounds of Formula I are prepared as follows:

EXAMPLE 1b

4-Methyl-5-[2-(4-phenyl-1-piperazinyl)ethyl]-2-thiazolamine, mp 186°–190° C.; and EXAMPLE 1c 4-[3-(4-Phenyl-1-piperazinyl)propyl]-2-thiazolamine; 112°–114° C.

EXAMPLE 1d

5-[2-(3,6-Dihydro-4-phenyl-1(2H)-pyridinyl]ethyl]-4-methyl-2-thiazolamine, containing ¾ of a mole of water; mp 173°–175° C. and EXAMPLE 1e 4-[3-(3,6-Dihydro-4-phenyl-1(2H)-pyridinyl)propyl]-2-thiazolamine, dihydrochloride; mp 252°–254° C.

EXAMPLE 1f

4-Methyl-5-[2-4-(2-pyrimidinyl)-1-piperazinyl]ethyl]-2-thiazolamine; mp 158°–162° C. and EXAMPLE 1g 4-[3-[4-(2-Pyrimidinyl)-1-piperazinyl]propyl]-2-thiazolamine; mp 154°–159° C.

EXAMPLE 1h

4-Methyl-5-[2-[4(2-pyridinyl)-1-piperazinyl]ethyl]-2-thiazolamine, hemihydrate; mp 135°–150° C. and EXAMPLE 1i 4-[3-[4-(2-Pyridinyl)-1-piperazinyl]-propyl]-2-thiazolamine, containing ¼ of a mole of water; mp 132°–137° C.

EXAMPLE 1j

4-Methyl-5-[3-[4-(2-pyridinyl)-1-piperazinyl]propyl]-2-thiazolamine, containing ⅓ of a mole of water; mp 150°–153° C. (dec) and EXAMPLE 1k 4-[4-[4-(2-Pyridinyl)-1-piperazinyl]butyl]-2-thiazolamine; mp 105°–110° C.

EXAMPLE 2

5-[2-4-(2-Pyridinyl)-1-piperazinyl]ethyl]-2-thiazolamine

A mixture of 5.84 g of 5-(2-chloroethyl)-2thiazolamine, monohydrochloride (Example C), and 5.27 g of 1-(2-pyridyl)piperazine in 100 ml of dimethylformamide containing 12.3 g of sodium bicarbonate is stirred at 80°–90° C. for 18 hours. The mixture is filtered and the filtrate concentrated to dryness. Chromatography (medium-pressure liquid chromatography, silica gel, 5% methanol-95% chloroform) of the resulting oil affords 5-[2-[4-(2-pyridinyl)-1-piperazinyl]ethyl]-2-thiazolamine as a tan solid; mp 158°–161° C.

EXAMPLE 2a

5-[2-(4-Phenyl-1-piperazinyl)ethyl]-2-thiazolamine

In a process analogous to Example 2, using appropriate starting materials, the title compound is prepared as a light tan solid; mp 185°–189° C.

EXAMPLE 2b

5-[2-(3,6-Dihydro-4-phenyl-1(2H)-pyridinyl)ethyl]-2-thiazolamine containing ¼ mole of water; mp 178°–186° C.

PREPARATIVE EXAMPLES FOR INTERMEDIATES

EXAMPLE A

6-[4-(2-Pyrimidinyl)-1-piperazinyl]-2-hexanone

A solution of 17.9 g of 6-bromo-4-hexanone and 23.7 g of 1-(2-pyrimidinyl)piperazine dihydrochloride in 500 ml of ethanol and 100 ml of dimethylformamide containing 42 g of sodium bicarbonate is refluxed for 12 hours. The mixture is filtered through Celite, evaporated in vacuo, and the residue chromatographed over silica gel to give 15 g of 6-[4-(2-pyrimidinyl)-1-piperazinyl]-2-hexanone; mp 44°–47° C.

EXAMPLE B

2-Amino-5-thiazoleethanol, Monohydrochloride

To an ice cold suspension of 118.2 g of N-bromosuccinimide in 750 ml of water under a nitrogen atmosphere is added dropwise 75 ml of 2,3-dihydrofuran. The resulting solution is stirred at 0° C. for one hour. Thiourea, 50.5 g, is added and the solution refluxed under a nitrogen atmosphere overnight. The acidic solution is continuously extracted with ethyl acetate for 24 hours The ethyl acetate extract contains mostly succinimide. The aqueous phase is basified with concentrated ammonium hydroxide to a pH of 10–11 and continuously extracted with ethyl acetate for 72 hours. The ethyl acetate extract is cooled and acidified with ethereal hydrogen chloride. The hydrochloride salt oils out of solution and is crystallized from an ethanol-acetonitrile mixture to give 60.1 g of 2-amino-5-thiazoleethanol as the monohydrochloride salt; mp 125°–127° C. (lit. (a) mp 126°–127° C.) lit. (a) *Farmaco. Ed. Sci.,* Vol. 41, pages 483–498 (1986).

EXAMPLE C 5-(2-Chloroethyl)-2-thiazolamine, Monohydrochloride

To a suspension of 14.73 g of 2-amino-5-thiazoleethanol, monohydrochloride (Example B) in 200 ml of chloroform is added rapidly 50 ml of thionyl chloride. The mixture is refluxed for 30 minutes, cooled to room temperature, filtered through a pad of Celite, concentrated to a brown oily solid, and crystallized from ethanol-diethyl ether to give 5-(2-chloroethyl)-2-thiazolamine as the monohydrochloride salt; mp 145°–147° C.

We claim:

1. A compound of Formula I

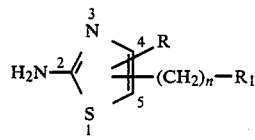

I wherein R is hydrogen or lower alkyl; n is an integer from 2 to 5; $R_1$ is

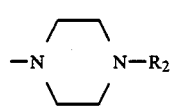

wherein $R_2$ is 2-, 3-, or 4-pyridinyl or 2-, 3-, or 4-pyridinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen; and either R or —(CH$_2$)$_n$—R$_1$ is attached at the 4 or 5 position; or a pharmaceutically acceptable acid addition salt thereof.

2. A compound according to claim 1 in which n is an integer from 2 to 4, R is hydrogen, methyl or ethyl, and $R_1$ is

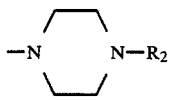

3. A compound according to claim 2 in which $R_2$ is 2-pyridinyl

4. A compound according to claim 3, and being 4-methyl-5-[2-[4-(2-pyridinyl)-1-piperazinyl]-ethyl]-2-thiazolamine.

5. A compound according to claim 3, and being 4-methyl-5-[3-[4-(2-pyridinyl)-1-piperazinyl]-propyl]-2-thiazolamine.

6. A compound according to claim 3, and being 4-[4-[4-(2-pyridinyl)-1-piperazinyl]butyl]-2-thiazolamine.

7. A compound according to claim 3, and being 4-[3-[4-(2-pyridinyl)-1-piperazinyl]propyl]-2-thiazolamine.

8. A compound according to claim 3, and being 5-[2-[4-(2-pyridinyl)-1-piperazinyl]ethyl]-2-thiazolamine.

9. A method of treating schizophrenia comprising administering to a host suffering therefrom a therapeutic effective amount of a compound of Formula I

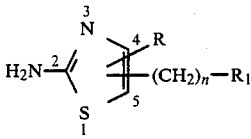

wherein R is hydrogen or lower alkyl; n is an integer from 2 to 5; $R_1$ is

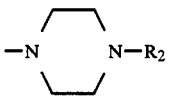

wherein $R_2$ is 2-, 3-, or 4-pyridinyl or 2-, 3-, or 4-pyridinyl substituted by lower alkyl, by lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen; and either R or $-(CH_2)_n-R_1$ is attached at the 4 or 5 position; or a pharmaceutically acceptable acid addition salt thereof.

10. A pharmaceutical composition adapted for administration as an agent for treating schizophrenia comprising a therapeutic effective amount of a compound according to claim 1 in admixture with a pharmaceutically acceptable excipient, diluent or carrier.

* * * * *

UNITED STATES PATENT AND TRADEMARK OFFICE
CERTIFICATE OF CORRECTION

PATENT NO. : 4,935,424
DATED : June 19, 1990
INVENTOR(S) : Bradley W. Caprathe, et al It is certified that error appears in the above—identified patent and that said Letters Patent is hereby corrected as shown below:

In Claim 9, at column 16, line 25
    insert after thereof --in unit dosage form--

Signed and Sealed this

Twenty-third Day of July, 1991

Attest:

HARRY F. MANBECK, JR.

Attesting Officer

Commissioner of Patents and Trademarks